(12) United States Patent
Selover et al.

(10) Patent No.: US 9,005,118 B2
(45) Date of Patent: *Apr. 14, 2015

(54) ILLUMINATED SURGICAL ACCESS SYSTEM INCLUDING A SURGICAL ACCESS DEVICE AND COUPLED LIGHT EMITTER

(75) Inventors: Sean Selover, Westport, MA (US); Sara Dziedzic, North Attleboro, MA (US); Steve Connolly, Sharon, MA (US); Sheryl Frank, Taunton, MA (US); Lorenzo Vaccarella, Woonsocket, RI (US)

(73) Assignee: Depuy Synthes Products, LLC, Raynham, MA (US)

( * ) Notice: Subject to any disclaimer, the term of this patent is extended or adjusted under 35 U.S.C. 154(b) by 106 days.

This patent is subject to a terminal disclaimer.

(21) Appl. No.: 12/899,699

(22) Filed: Oct. 7, 2010

(65) Prior Publication Data
US 2011/0021882 A1 Jan. 27, 2011

Related U.S. Application Data

(63) Continuation of application No. 11/265,902, filed on Nov. 2, 2005, now Pat. No. 7,874,982.

(51) Int. Cl.
| | | |
|---|---|---|
| *A61B 1/32* | (2006.01) | |
| *A61B 17/02* | (2006.01) | |
| *A61B 17/34* | (2006.01) | |
| *A61B 19/00* | (2006.01) | |

(52) U.S. Cl.
CPC ............ *A61B 17/02* (2013.01); *A61B 17/3421* (2013.01); *A61B 17/3423* (2013.01); *A61B 2019/5206* (2013.01)

(58) Field of Classification Search
USPC .................. 600/199, 200, 245, 246; 362/551, 362/572–574, 632
See application file for complete search history.

(56) References Cited

U.S. PATENT DOCUMENTS

| | | |
|---|---|---|
| 3,774,596 A | 11/1973 | Cook |
| 4,181,123 A | 1/1980 | Crosby |

(Continued)

FOREIGN PATENT DOCUMENTS

| | | |
|---|---|---|
| DE | 19732785 A1 | 2/1999 |
| JP | 2001-104323 | 4/2001 |

(Continued)

OTHER PUBLICATIONS

Japanese Office Action for Application No. 2008-538999, dated Sep. 27, 2011.

(Continued)

*Primary Examiner* — Mary Hoffman
(74) *Attorney, Agent, or Firm* — Nelson Mullins Riley & Scarborough LLP

(57) ABSTRACT

A surgical access system for providing access to a surgical site in a patient includes a surgical access device defining a port and a light emitter coupled to the surgical access device for illuminating the port. The light emitter preferably comprises an elongated shaft having a light transmitting element housed therein, which emits light transmitted to the elongated shaft from a light source. The elongated shaft is configured to be inserted in an elongated channel in the access device. The elongated channel has or forms a window for transmitting light emitted by the light emitter into the interior of the access device.

9 Claims, 15 Drawing Sheets

(56) References Cited

U.S. PATENT DOCUMENTS

| | | | |
|---|---|---|---|
| 4,215,678 | A | 8/1980 | Heine et al. |
| 4,449,519 | A | 5/1984 | Sarrine |
| 4,562,832 | A | 1/1986 | Wilder et al. |
| 4,852,549 | A | 8/1989 | Mori |
| 5,000,535 | A | 3/1991 | Churchill |
| 5,050,047 | A | 9/1991 | Viner et al. |
| 5,165,387 | A | 11/1992 | Woodson |
| 5,179,938 | A | 1/1993 | Lonky |
| 5,353,786 | A | 10/1994 | Wilk |
| 5,785,648 | A | 7/1998 | Min |
| 6,010,531 | A | 1/2000 | Donlon et al. |
| 6,017,142 | A | 1/2000 | Harris, Jr. |
| 6,241,658 | B1 | 6/2001 | Goodrich |
| 6,551,346 | B2 | 4/2003 | Crossley |
| 6,616,603 | B1 | 9/2003 | Fontana |
| 6,717,824 | B2 | 4/2004 | Miyajima et al. |
| 6,939,296 | B2 | 9/2005 | Ewers et al. |
| 7,150,714 | B2 | 12/2006 | Myles |
| 7,371,213 | B2 | 5/2008 | Hestad et al. |
| 7,503,894 | B2 | 3/2009 | Vankoski et al. |
| 7,556,601 | B2 | 7/2009 | Branch et al. |
| 7,708,688 | B2 | 5/2010 | Welker et al. |
| 2004/0143167 | A1 | 7/2004 | Branch et al. |
| 2004/0143169 | A1 | 7/2004 | Branch et al. |
| 2004/0230100 | A1 | 11/2004 | Shluzas |
| 2005/0165283 | A1* | 7/2005 | Hestad et al. ............... 600/212 |
| 2005/0203341 | A1 | 9/2005 | Welker et al. |
| 2005/0277811 | A1* | 12/2005 | Richards et al. ............. 600/184 |
| 2006/0069313 | A1 | 3/2006 | Couvillon et al. |
| 2006/0069314 | A1 | 3/2006 | Farr |
| 2007/0043264 | A1* | 2/2007 | Gillis et al. ................. 600/184 |

FOREIGN PATENT DOCUMENTS

| | | |
|---|---|---|
| JP | 2002-514127 | 5/2002 |
| WO | 2005/060837 A2 | 7/2005 |

OTHER PUBLICATIONS

European Office Action for Application No. 06827285.5, dated Sep. 3, 2009.
International Search Report for Application No. PCT/US06/42659, dated Aug. 9, 2007.
Supplementary European Search Report for Application No. 06827285.5, dated May 29, 2009.
Australian Office Action for Application No. 2006312057, dated Apr. 11, 2011.
Japanese Office Action for Application No. 2008-538999, 2 pages, dated May 22, 2012.
Canadian Office Action for Application No. 2,628,373, 2 pages, dated Dec. 9, 2013.

* cited by examiner

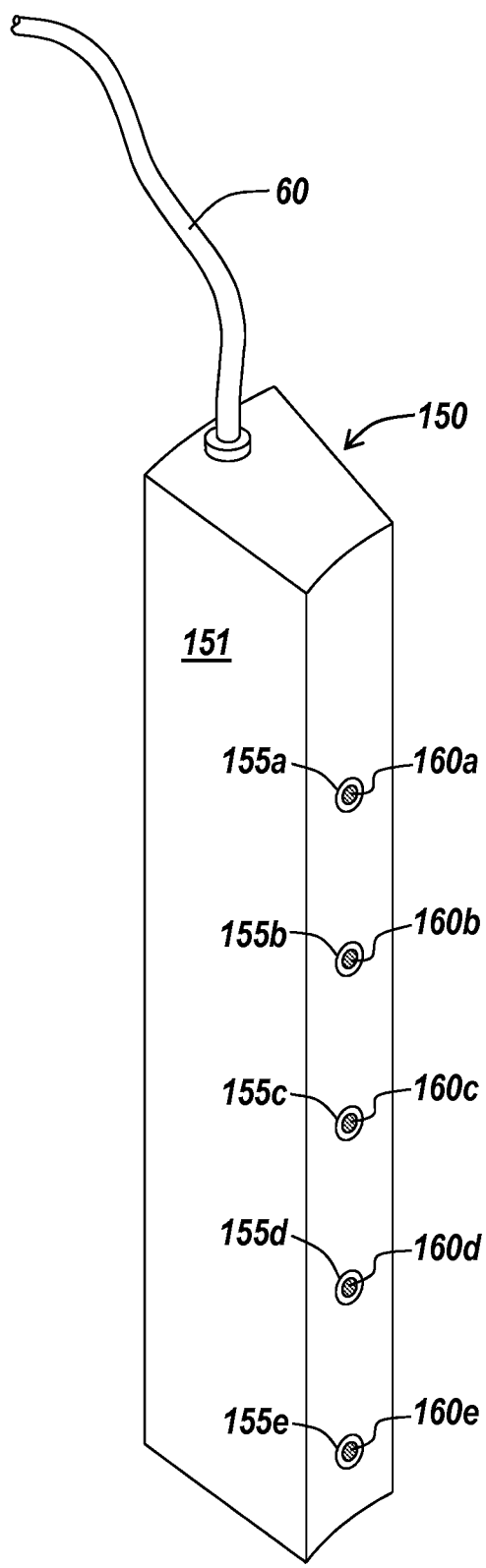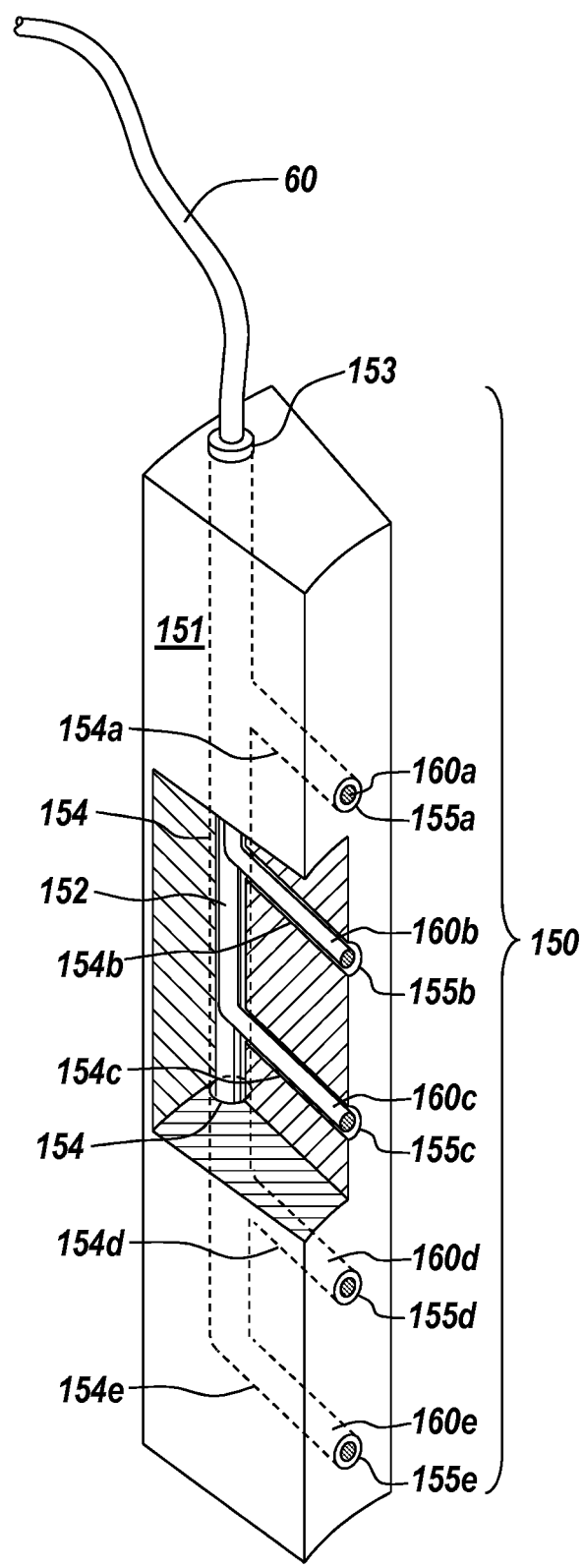
*Fig. 2A*  *Fig. 2B*

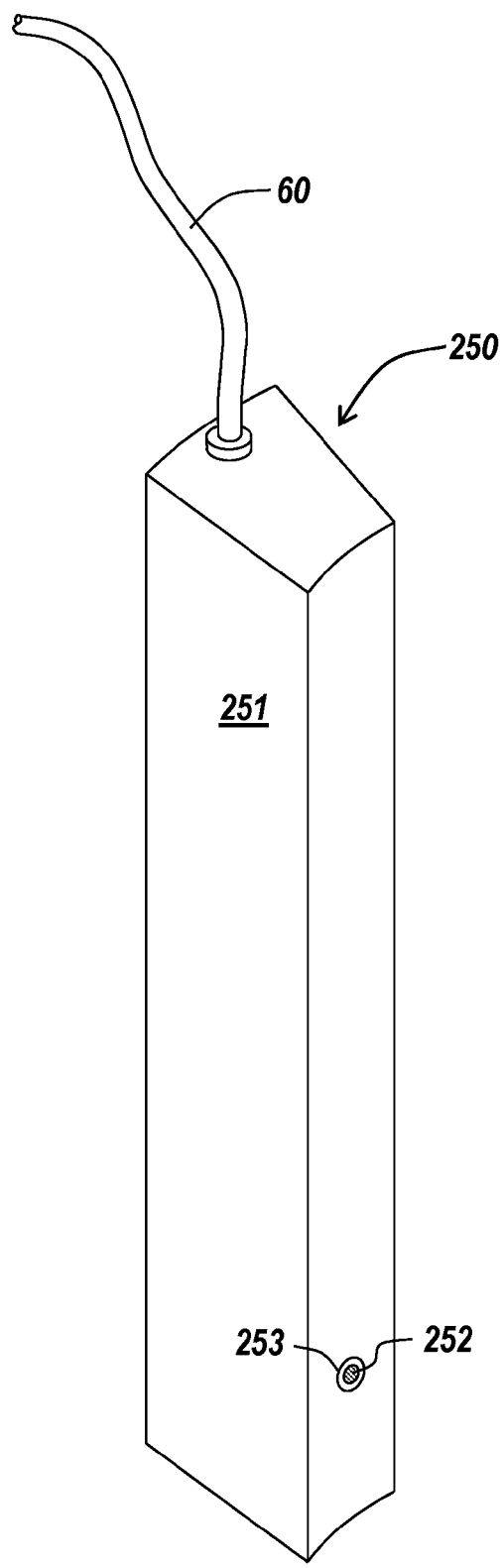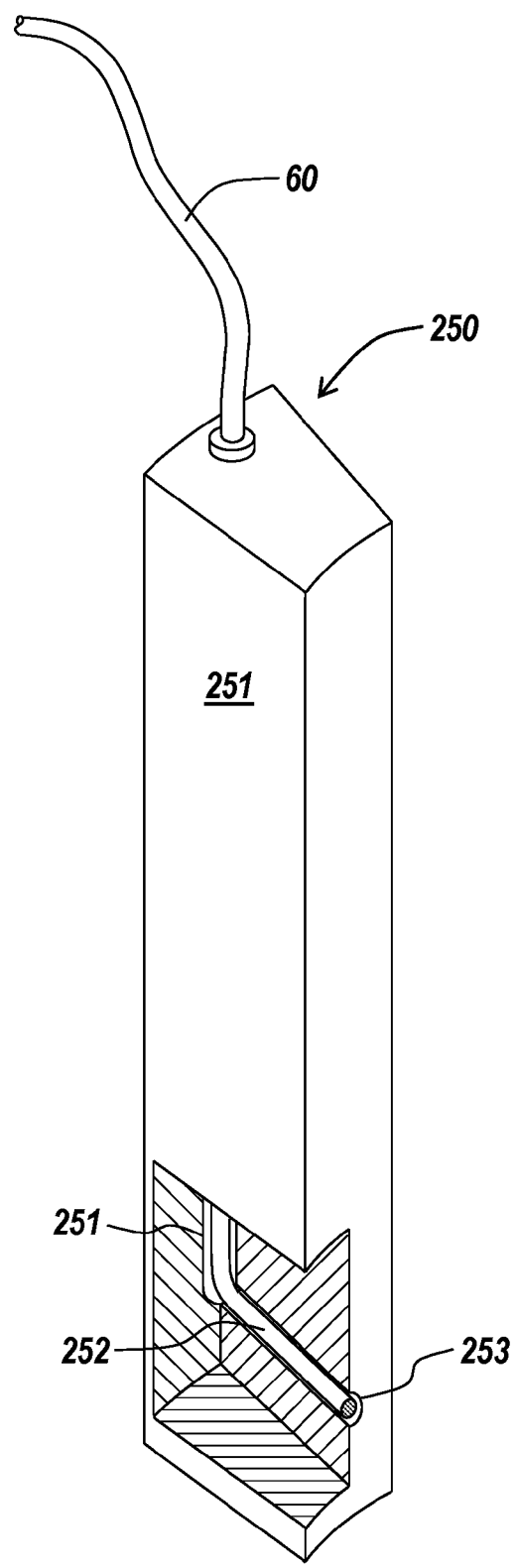
*Fig. 5A*  *Fig. 5B*

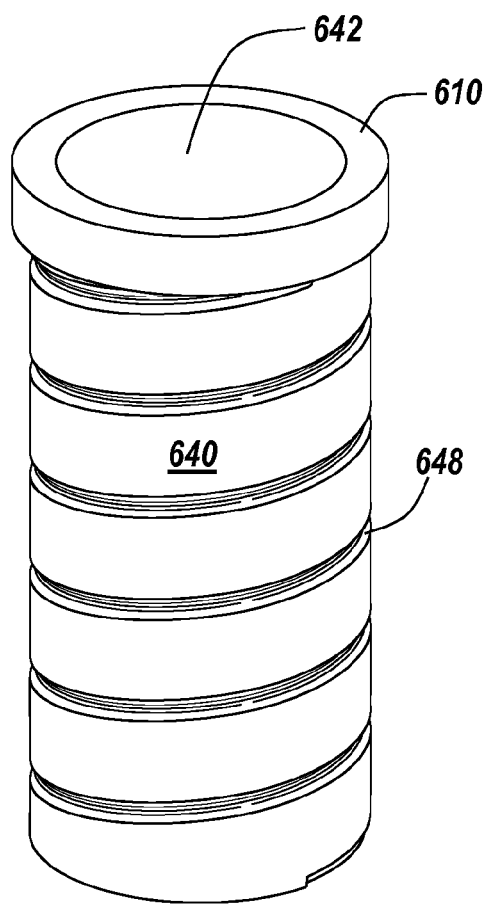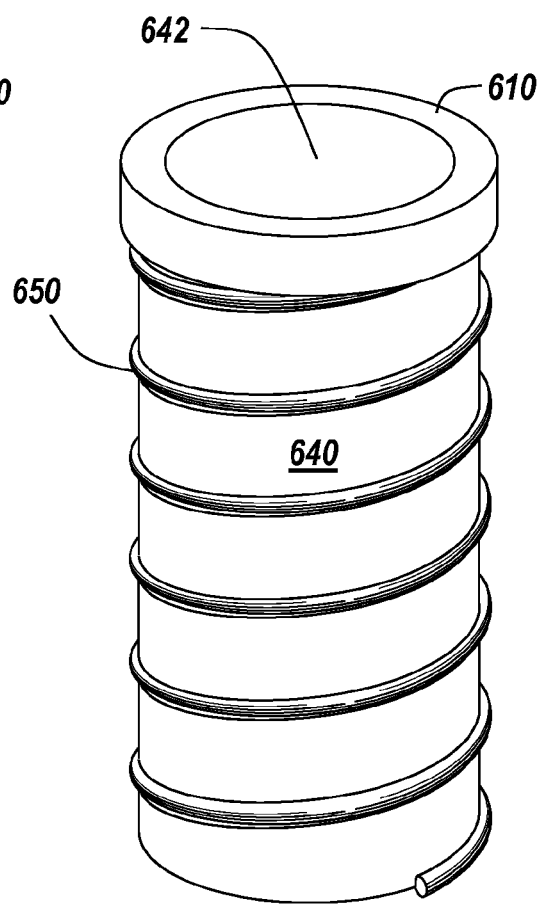
*Fig. 12A*  *Fig. 12B*

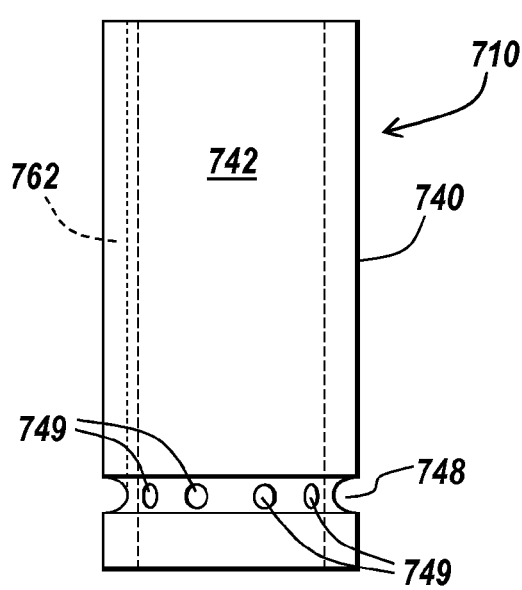
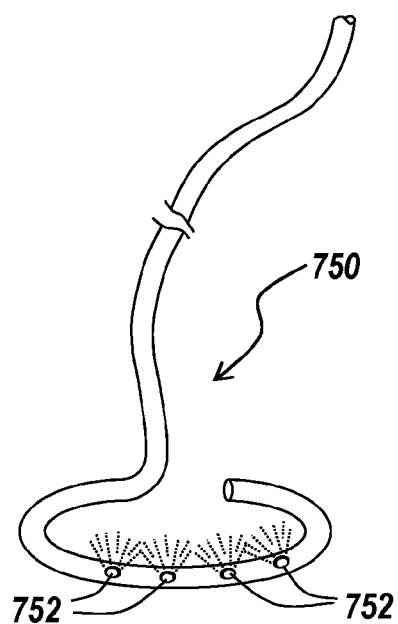
Fig. 14A    Fig. 14B
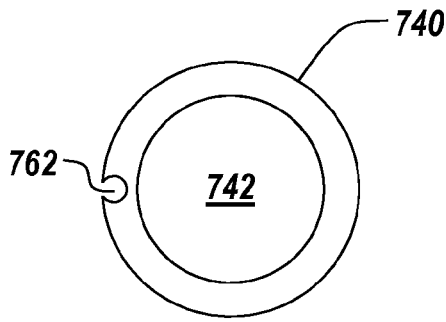
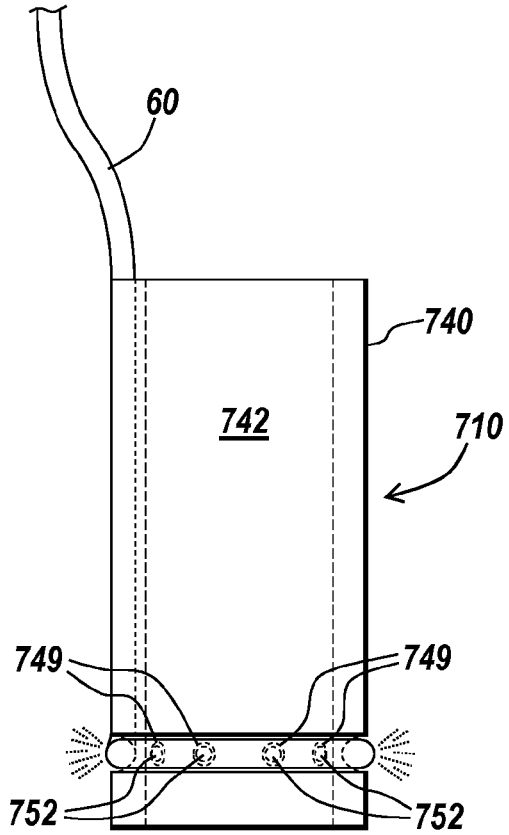
Fig. 14C    Fig. 14D

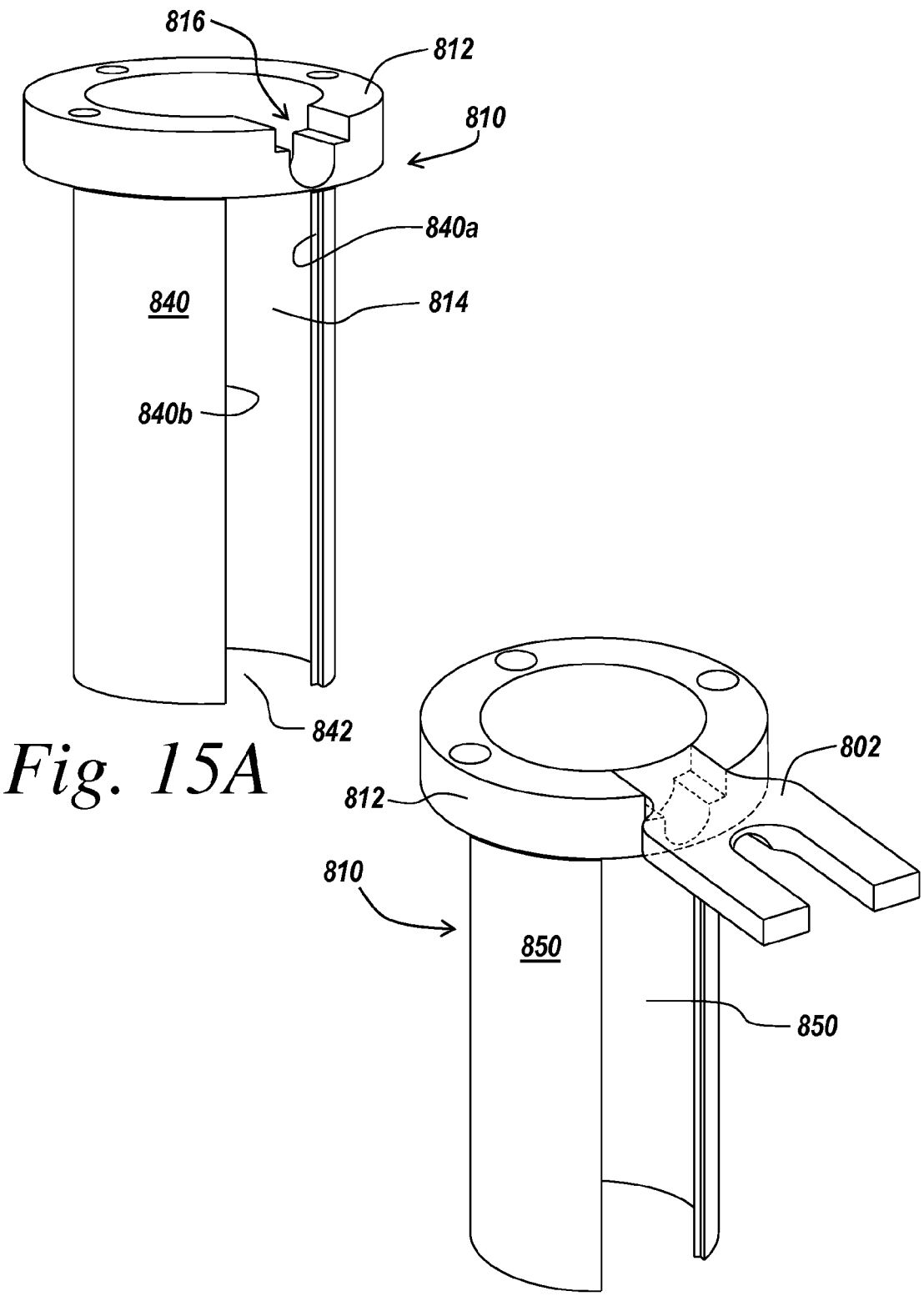

ILLUMINATED SURGICAL ACCESS SYSTEM INCLUDING A SURGICAL ACCESS DEVICE AND COUPLED LIGHT EMITTER

RELATED APPLICATION

This application is a continuation application of U.S. patent application Ser. No. 11/265,902, entitled "ILLUMINATED SURGICAL ACCESS SYSTEM INCLUDING A SURGICAL ACCESS DEVICE AND COUPLED LIGHT EMITTER," filed Nov. 2, 2005, now U.S. Pat. No. 7,874,982, the contents of which are hereby incorporated by reference.

FIELD OF THE INVENTION

The present invention relates to devices used in surgery. More particularly, the present invention relates to instrumentation and a method for the providing access and illumination for surgical sites, implements and implants.

BACKGROUND OF THE INVENTION

In invasive surgical procedures, illumination of a working space may be required to facilitate use of the surgical instruments. For example, in spinal surgery, access ports, comprising generally tubular, open-ended structures, are often used to provide access to a surgical site. The access ports may require illumination at the distal end thereof to facilitate the surgical procedure.

Achieving proper illumination of a surgical site during minimally invasive surgery can be difficult. In the current state of the art, external light sources are used to provide illumination to access ports. However, external light sources are unwieldy, and the link used to transmit the generated light to the access port can be cumbersome and block access by a surgeon to the port. For example, a surgeon may wear a head-mounted light in order to illuminate the working area at the base of an access port. Head-mounted light sources may require the surgeon to constantly direct the light with his or her head at an optimal angle, into the access port in order to view the working area. In addition, fiber optic cables, attached to the light, can encumber the surgeon and tether him or her to a light source.

Another option currently used by surgeons involves lights mounted on an overhead microscope. When surgeons use an overhead microscope to illuminate a surgical space, the light source is distant from the surgical site, increasing the likelihood of creating shadows and potentially obstructing the ability of the light to reach the working area.

Other alternatives for lighting a surgical site place small light sources into the interior of an access port to illuminate the work space. However, the use of a light source within the access port can reduce the available working area in the port, and may hinder the use of instruments that enter and exit the port during surgery.

SUMMARY OF THE INVENTION

The present invention provides an illuminated surgical access system including a light emitter coupled to a surgical access device. The surgical access device defines a path or port to a surgical site and the light emitter emits and directs light into and along the path to illuminate a surgical site accessed by the surgical access device. The light emitter may have an elongated shaft having light transmitters, such as fiber optic cables connected to a light source, that terminate along the elongated shaft to emit light from the shaft. The elongated shaft is configured to be inserted in an elongated channel on the surgical access device. The elongated channel has a window or other opening to the interior of the surgical access device, so that light emitted from the light-emitting shaft passes to the interior of the surgical access device and is directed to a working area at a distal tip of the surgical access device closest to the body. The integrated light emitter does not reduce the working area of the access device or hinder the surgeon, while providing superior illumination of a surgical site.

According to a first aspect of the invention, an illuminated surgical access system for providing access to a patient during surgery is provided. The illuminated surgical access system comprises a surgical access device comprising at least one sidewall, defining an interior path forming a port for accessing the patient and an elongated channel formed on the side wall and an elongated light-emitting shaft inserted in the elongated channel. The elongated light-emitting shaft includes a light transmitting element for emitting light to illuminate the port of the access device.

According to another aspect of the invention, a light emitter for a surgical access system is provided. The light emitter comprises an annular base, a plurality of protruding shafts extending from the base, the plurality of protruding shafts distributed about the perimeter of the annular base and a plurality of fiber optic cables extending from a light source to the annular base. A subset of the fiber optic cables branch from the annular base through each protruding shaft and terminate at an outlet of the respective protruding shaft so as to emit light therefrom.

According to another aspect of the invention, a light emitter for a surgical access system comprises a housing in the shape of an elongated shaft, a branched path extending through the housing, the branched path having an inlet and a plurality of outlets and a bundle of fiber optic cables passing through the branched path. The bundle of fiber optic cables branches off into branches, with a subset of the fiber optic cables passing through a branch of the path and terminating at the outlet to emit light transmitted through the subset of the fiber optic cables.

According to still another aspect of the invention, a tubular surgical access device for accessing a surgical site is provided. The tubular surgical access device includes a tubular body having a side wall and defining a path therethrough forming a port for accessing the patient, an elongated channel formed on the side wall of the tubular body and a window formed in the elongated channel for interfacing the elongated channel with the path through the tubular body.

According to another aspect, a method of accessing a surgical site in a patient comprises the steps of providing a surgical access device comprising at least one sidewall having an elongated channel and defining a path therethrough forming a port for accessing the patient and inserting an elongated light-emitting shaft into the elongated channel.

BRIEF DESCRIPTION OF THE FIGURES

These and other features and advantages of the present invention will be more fully understood by reference to the following detailed description in conjunction with the attached drawings in which like reference numerals refer to like elements through the different views. The drawings illustrate principals of the invention and, although not to scale, show relative dimensions.

FIGS. 2A and 2B illustrates an embodiment of a light-emitting shaft for a surgical access system according to an illustrative embodiment of the invention.

FIGS. 5A and 5B illustrates another embodiment of a light-emitting shaft including a single light emission point suitable for use in an illuminated surgical access system of the invention.

FIGS. 12A and 12B illustrate an embodiment of an elongated light emitter having a helical configuration and a corresponding surgical access device.

FIGS. 14A-14D illustrate an embodiment of an elongated light emitter having an annular configuration and a corresponding surgical access device.

FIGS. 15A-15B illustrate an elongated light emitter and corresponding surgical access device where the light emitter forms a portion of the side wall of the surgical access device according to another embodiment of the invention.

DETAILED DESCRIPTION OF THE INVENTION

The present invention provides an improved surgical access system for accessing a surgical site during surgery including an integrated light emitter for illuminating the surgical site and/or a path to the surgical site. The present invention will be described below relative to certain illustrative embodiments. Those skilled in the art will appreciate that the present invention may be implemented in a number of different applications and embodiments and is not specifically limited in its application to the particular embodiments depicted herein.

The illuminated surgical access system of the illustrative embodiment of the invention may be used in spinal surgery, for example, during a discectomy or microdiscectomy procedure to remove damaged disc material from the spine, though one skilled in the art will recognize that the invention can be used with any surgical instrument in any surgical procedure that requires illumination. Examples of surgical procedures suitable for employing the illuminated surgical access system of the present invention include, but are not limited to, insertion of interbody fusion devices, bone anchors, fixation devices, including rods, plates and cables, artificial disks, hip stems, artificial ligaments, trochars for gastro-intestinal work, or any procedure requiring access to a patient as well as visualization. The surgical access system may be part of any suitable implant instrument used to provide access to a particular area of a patient's body where visualization is also needed. The surgical access system can be used to position any suitable implant, instrument and/or other device in any suitable procedure where guidance of the implant, instrument and/or device is used. Alternatively, or in addition to providing guidance, the surgical access system may be used to dilate a surgical incision using a set of progressively larger cannulas or an expanding cannula to provide access to a surgical site.

Figure 1:
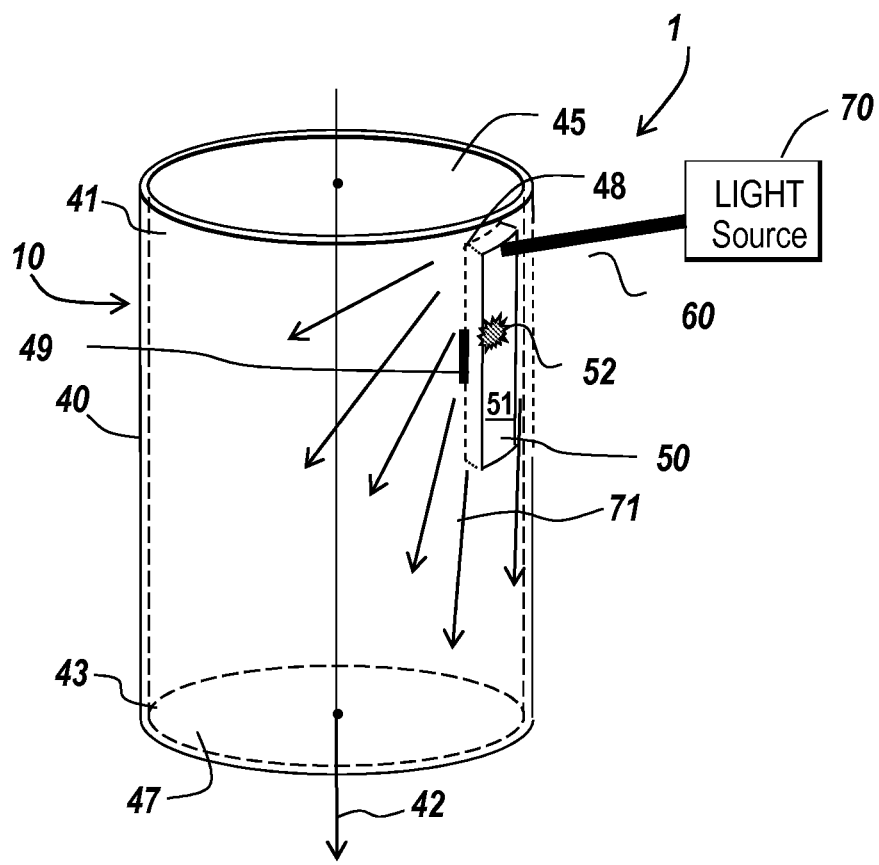
FIG. 1 illustrates an illuminated surgical access system including a light emitter comprising a light-emitting shaft according to an embodiment of the invention.

Referring to FIG. 1, an illuminated surgical access system 1 of an illustrative embodiment of the invention includes a surgical access device 10 for accessing a surgical site and a light emitter 50 coupled to the access device 10 for providing illumination to the surgical site during performance of a surgical procedure. In the illustrative embodiment, the light emitter 50 comprises an elongated shaft that emits light and is coupled to the access device 10. Preferably, the light emitter 50 is held in a channel, which may be an opening, slot, lumen, groove, or other suitable channel, formed in the body of the access device 10, as described in detail below. An intermediate light transmitter, illustrated as a light transmitting cable 60, transmits light from a light source 70 to the light emitter 50, which emits the light 71 into the path of the access device 10.

The illustrative access device 10 may be a standard access port, in the shape of a cannula comprising a hollow tubular body suitable for insertion in and/or placement adjacent to a patient's body. The illustrative access device 10 has at least one hollow central channel or lumen defining a path 42 extending from an open proximal end 41 of the access device to an open distal end 43 of the access device. The path 42 may form a working channel or at least a portion of a working channel for accessing a surgical site adjacent to or in the vicinity of the distal end 43 of the tubular body. In the illustrative embodiment, the body of the access device 10 includes open proximal end 41 that forms a proximal port 45, and the open distal end 43 forms a distal port 47 for allowing access to the surgical site. One skilled in the art will recognize that the access device 10 may have any suitable configuration and size for providing access to an area of a body. The illustrative access device may be used for retaining soft tissue away from a surgical site and/or guiding a surgical instrument, device and/or implant, though one skilled in the art will recognize that the access device may comprise any suitable device defining a path or channel requiring illumination.

As shown, the tubular body of the illustrative access device 10 is formed by a cylindrical sidewall 40, though one skilled in the art will recognize that the tubular body can have any size, shape, configuration and number of sidewalls. The access device can be any suitable device defining a port for providing access to a surgical site. The access device can have any suitable cross-section and is not limited to the cylindrical cross-section shown in the illustrative embodiments. The access device can be open or closed to define an open or closed path 42 therethrough.

The access device can be formed of any suitable surgical material, such as, but not limited to, plastic, surgical stainless steel and other materials known in the art.

The tubular body includes at least one elongated channel 48 formed on or in the side wall 40 for receiving the elongated light emitter 50. The light emitter 50 couples to the tubular body 40 to transfer and emit light 71 produced by a light source 70 to illuminate the path 42 and/or the distal port 47 at the distal end 43 of the access device 10.

Preferably, the light emitter 50 is inserted in the elongated channel 48 in the housing of the access device 10 to couple the light emitter 50 to the housing. The channel 48 preferably has a shape that matches the shape of the light emitter 50. The channel 48 includes at least one window 49, comprising a transparent portion interfacing the channel 48 with the interior path 42 of the access device, to allow transmission of light from the light emitter 50 to the interior of the access device, as described in detail below. The window 49 may comprise an opening in the side wall 40 of the access device 10 adjacent the outlet of the light emitter 50, or may be formed of transparent material adjacent the outlet. Any suitable translucent means, including air, may form the window 49.

The window may cover the entire length of the channel 48, or only selected portions of the channel 48.

Preferably, the light emitter 50 may be removably coupled to the access device 10, so that the light emitter 50 may be easily used with a variety of different access devices and/or removed to facilitate cleaning.

Preferably, the light emitter 50 comprises a housing 51, which may be in the shape of an elongated shaft, and at least one light transmission element 52 disposed in the housing for emitting light. In the illustrative embodiment, the light transmission element 52 comprises a plurality of fiber optic strands extending from the light source 70 through the intermediate light transmitter 60 to the housing 51 to transmit light generated by the light source 70 to the housing 51. As described below, the housing 51 preferably includes an inlet for receiving the light transmission element or an intermediate light transmitter that delivers light to the light transmission element, and at least one outlet for emitting light from the light transmission element 52.

The housing 51 may be formed of any suitable surgical material, such as, but not limited to, plastic, epoxy, surgical stainless steel, titanium, ceramics, and other materials known in the art.

The light transmission element 52 may comprise glass fiber optic cables, plastic fiber optic cables or any other suitable means for transmitting and emitting light.

As shown, the intermediate light transmitter 60 is a cable that bundles the transmission elements 52 in the region between the light source 70 and the light emitter housing 51. Alternatively, a separate transmission means may be used to transmit light from the light source 70 to the light transmission element 52 in the housing 51.

The light source 70 may be any suitable device for producing light, including, but not limited to, halogen light boxes, incandescent light boxes and other light sources readily available in most hospital settings, such as those available from Welch Allyn Medical Products of Skaneateles Falls, N.Y. The light source may have any suitable power level. In an illustrative embodiment, the light source is a 300 Watt Halogen Light Box. Any other suitable light source capable of producing light that is transmitted via the light transmitters, such as fiber optic cables, may also be used.

FIGS. 2A and 2B illustrate one embodiment of an elongated light emitter suitable for use in an illuminated access system according to an illustrative embodiment of the invention. The light emitter 150 of FIGS. 2A and 2B comprises an elongated shaft 151 defining a branched path 154 therethrough, shown in FIG. 2B, for housing a bundle of fiber optic strands 152. The branched path 154 terminates in a plurality of outlets 155a-155e spaced along the length of the elongated shaft 151. The bundle of fiber optic strands 152 enters the elongated shaft 151 at an inlet 153 as a sheathed fiber optic cable 60, which is preferably connected to a light source that produces light, which is then transmitted through the fiber optic cable and through the fiber optic strands 152. Inside the casing, the fiber optic strands branch out into branches 160a-160e through branched paths 154a-154e and terminate at the outlets 155a-155e, respectively, where the light is emitted from the end each strand. The ends of the strands may be cut at a selected angle to direct light transmitted therethrough to a selected location and in a selected direction. In this manner, light is emitted along the length of the housing 151. Each branch 160a-160e of fiber optic strands may comprise one or several fiber optic strands.

Preferably, the outlets 155a-155e where light is emitted are equally spaced along the length of the shaft 151 to prevent shadows.

Alternatively, each fiber optic strand 152 may include a modified cladding or other suitable means at selected locations to provide light emission points along the length of the fiber optic strand. Each emission point preferably aligns with an outlet 155 and/or transparent portion of the housing of the light emitter 150 to allow light emission from the light emitter.

The ends of the fiber optic strands 152 may be polished and set in place within the outlets 155a-155e via any suitable means. For example, an epoxy may be used to seal and/or fix the fiber optic strands within the respective branch path 154.

In one embodiment, the housing 151 of the elongated light-emitting shaft 150 may comprise a transparent, semi-rigid, light-transferring medium that encases the fiber optic strands and/or the termination points of the fiber optic strands 152. When light is emitted from the end of a strand, the encased medium then reflects or scatters exiting light from each individual strand out of the shaft 150, creating a diffuse light source. For example, fiber optic strands may be coated in a suitable medium, such as an epoxy, which is then shaped to form the elongated light-emitting shaft 150 with branched paths 154.

In another embodiment, the housing 151 may be molded to define the branched path 154.

Figures 3, 4:
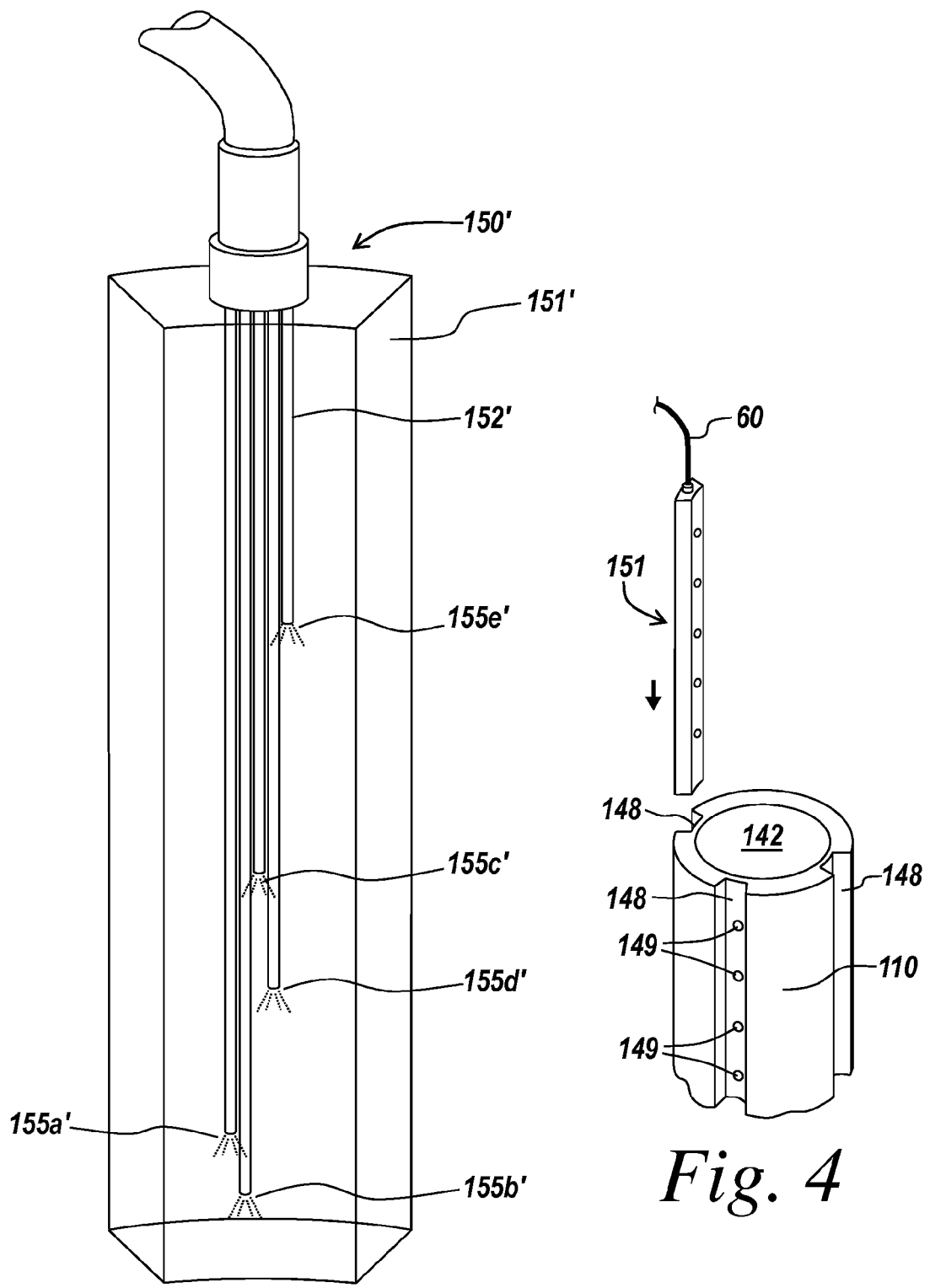
FIG. 3 illustrates another embodiment of a light-emitting shaft for a surgical access system according to an illustrative embodiment of the invention.
FIG. 4 illustrates a surgical access device suitable for use with the light-emitting shaft of FIGS. 2A and 2B and/or the light emitting-shaft of FIG. 3.

FIG. 3 illustrates another embodiment of a light-emitting shaft 150' including a plurality fiber optic strands terminating along a linear path according to another aspect of the invention. In the embodiment of FIG. 3, the shaft housing 151' comprises a transparent medium that encases a plurality of fiber optic strands 152'. The fiber optic strands 152' terminate at different heights along the length of the transparent housing 151'. Each fiber optic strand emits light from an emission point 155a', 155b', 155c', 155d' and 155e, which is illustrated as the termination point of the strand. The light is transmitted through the transparent medium, so that emit light is emitted along the length of the shaft 150'.

A corresponding surgical access device 110, shown in FIG. 4, includes at least one elongated channel, illustrated as a slot or a groove 148, for receiving the light emitter 150 to couple the light emitter 150 or 150' thereto. In the embodiment of FIG. 4, the elongated groove 148 comprises an open channel formed in the outer surface of the side wall 240 defining the access device 110. The illustrative groove 248 extends substantially parallel to the longitudinal axis of the access device internal working area. The groove 148 has an open proximal end extending to the top proximal end of the access device 110 to allow the light emitter 150 or 150' to slide into the groove, as shown in FIG. 4.

Alternatively, the elongated groove 148 may be a closed channel formed within the side wall, a channel formed in an interior surface of the side wall, or may comprise an elongated opening in the side wall, as described in certain additional embodiments below. The elongated channel 148 in the access device may have any suitable size, configuration and location suitable for receiving a light emitter, such as the light emitter 150 or 150'.

The access device 110 of FIG. 4 has a plurality of grooves 148 dispersed about the perimeter of the access device, with each groove 148 configured to receive a light-emitting shaft, such as the light emitter 150 or 150'. The access device may include any suitable number of grooves configured to receive light emitters.

As shown, each groove 148 includes at least one window 149 to the path 142 for transmitting light emitted from the light emitter 150 or 150' to the path 142. In the illustrative embodiment, each groove 148 includes a plurality of windows 149 at different heights along the length of the groove. Each window 149 preferably aligns with an outlet 155 or other light emission point of the light emitter 150 or 150' when the light emitter is inserted in the groove 148, so that light emitted from the outlets 155, 155' or other light emission point is transferred into the interior of the access device 110.

As shown, the illustrative light emitters 150 and 150' of FIGS. 2A-3 have a substantially wedge-shaped cross section to facilitate insertion of the light emitter in the corresponding groove 148 of the access device, while preventing the light emitter from falling out of the groove. The illustrative corresponding groove 148 in the access device 110 has a matching wedge shape to allow the light emitter 150 or 150' to slide therethrough to couple the light emitter to the access device. Alternatively, the light emitter 150 or 150' and corresponding groove 148 may have a circular, oval or other suitably shaped cross-section.

The angle of the wedge of the light emitter housing 151 or 151' be made to create a dovetail joint with the corresponding groove 148 running down the outer wall of the access device 10 to provide a track for the light emitter 150 or 150' to move along while maintaining a set alignment with the port 110.

When the light emitter 150 or 150' is coupled to the access device 110 and exposed to a light source, the terminating points of the fiber optic strands, or other light transmission elements employed by the light emitter, shine directional light through the windows 149 in the walls of the access device, illuminating the work area of the access device 110, without interfering with the working space.

FIGS. 5A and 5B illustrate another embodiment of an elongated light emitter 250 suitable for use in an illuminated surgical access system according to an illustrative embodiment of the invention. The light emitter 250 comprises an elongated shaft 251 forming a housing. The housing defines a single path 254 that turns and terminates at an outlet 253 for housing a light transmission element, such as a fiber optic cable 252 comprising one or more fiber optic strands. The outlet 253 is preferably located at a lower end of the shaft 251.

As described above, the outlet may include epoxy or another means for fixing the fiber optic cable 252. The housing may be a transparent medium and the outlet 253 may be open or comprise a transparent medium covering the end of the fiber optic cable.

Figure 6A:
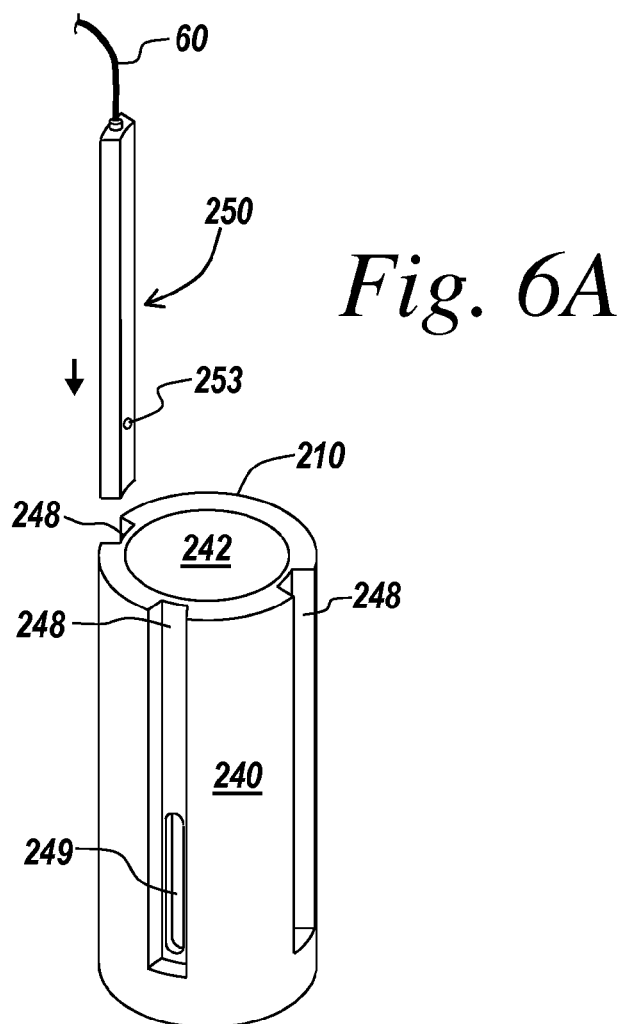
FIGS. 6A and 6B illustrate embodiments of surgical access devices suitable for use with the light-emitting shaft of FIGS. 5A and 5B.

A corresponding access device 210, shown in FIG. 6A, has one or more grooves 248 formed in the side wall 240 for receiving the elongated light emitter 250 to couple elongated light emitter to the access device 210. The illustrative grooves 248 each include at least one elongated window 249 interfacing the corresponding groove with the device interior path 242. The elongated window 249 allows adjustment of height of the light emitter 250 along the path length, while maintaining the light emitting outlet 253 of the light emitter 250 in alignment with at least a portion of the window 249, so that a user can adjust the direction of the emitted light according to his preference.

Figure 6B:
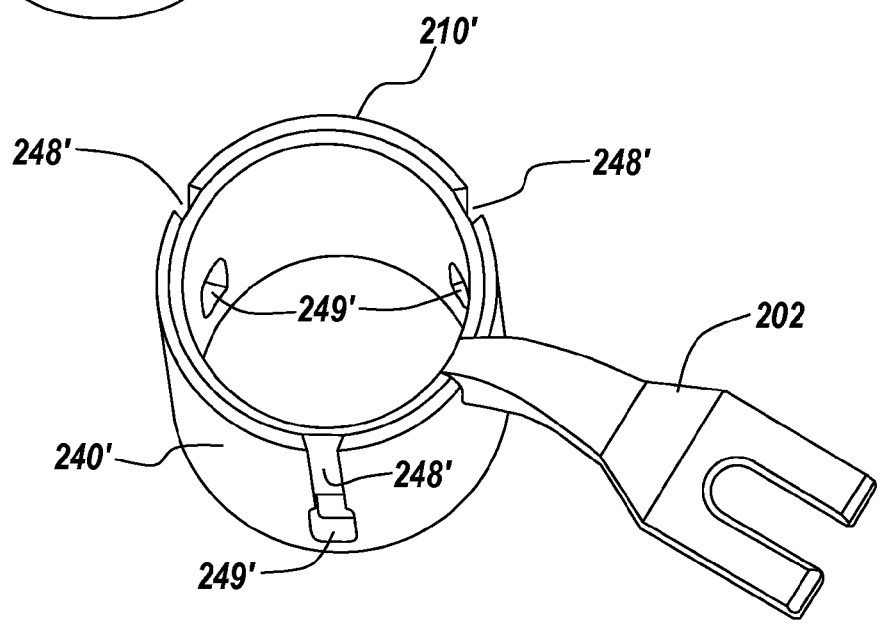

FIG. 6B is another embodiment of an access device 210' including an elongated window 249' in a groove 248' for receiving a light emitting shaft, such as the light emitting shaft 250 of FIGS. 5A and 5B. The access device 210' of FIG. 6B includes a rigid arm attachment 202 for attaching the access device 210' to a base or other suitable system for allowing positioning of the illuminated surgical access system relative to a selected surgical site.

According to another embodiment of the invention, shown in FIGS. 7A-9, an elongated light emitter comprising a light emitting shaft 350 may be inserted into a longitudinally extending a closed channel, illustrated as lumen 348 extending longitudinally through the side wall 340 of the access device 310, substantially parallel to the longitudinal axis path 342 of the access device. The access device 310 can have a plurality of longitudinally extending lumens 348 distributed about the periphery of the device for receiving a plurality of elongated rod-like light-emitters, such as the light emitter 350 shown in FIG. 8. Each longitudinally extending lumen 348 includes at least one window 349 configured to align with an emission point on the light emitter 350 to transfer light from the light emitter to a selected location. The window 349 preferably forms an interface to the access device interior 342.

Alternatively, or in addition, one or more windows 349' can be disposed at the distal end 370 of the side wall 340 to direct light longitudinally through the side wall 340 to the distal tip of the access device and to the surgical site.

A cover 360 may also be provided for closing the lumens 348 and retaining the elongated light emitters within the lumens. The illustrative cover 360 is ring-shaped, including an annular opening 361 and an annular body 362 that fits over the side wall of the access device. The cover 360 may also include protrusions 364 extending from the body 362 that are configured to be received in the top portion of each lumen 348 to close the lumens 348.

Figure 7A:
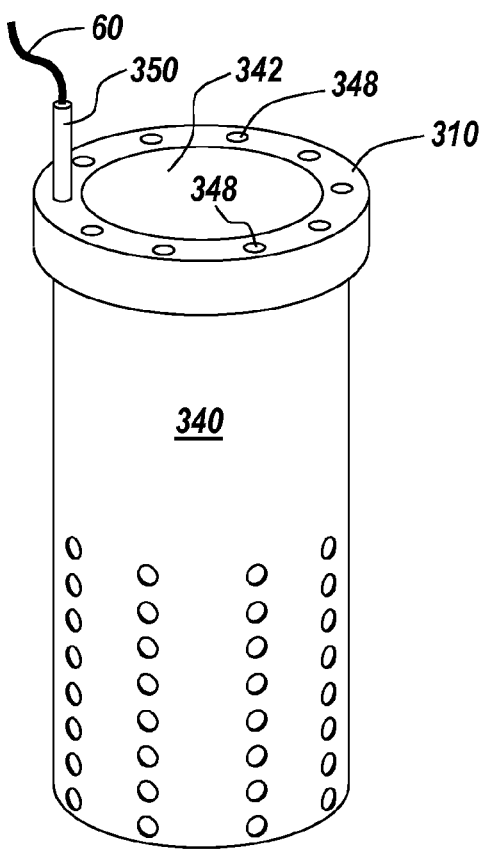
FIG. 7A-7C illustrate another embodiment of an illuminated surgical access system of the invention.
Figure 7B:
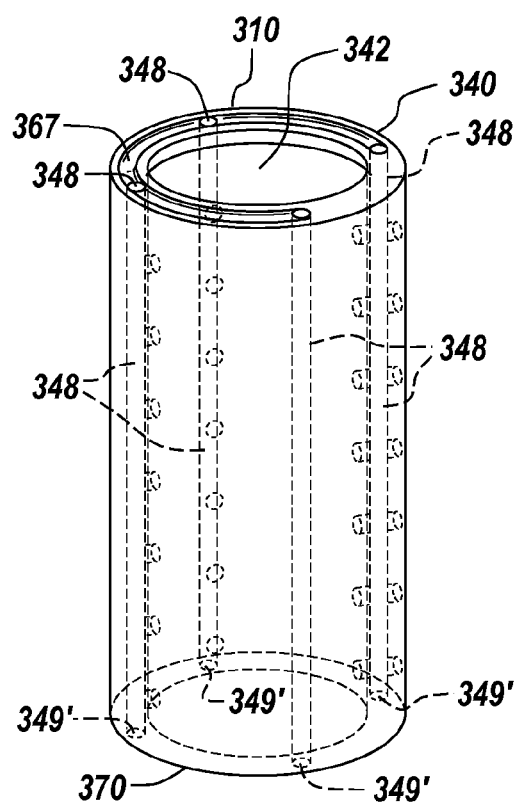
Figure 7C:
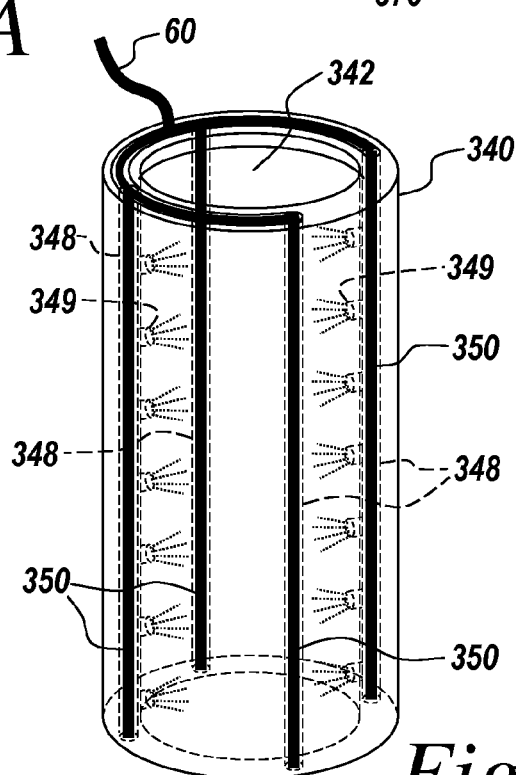

As shown in FIG. 7C, a plurality of elongated light emitters 350 may be connected to a single cable 60, which branches off to form each light emitter 350. The branching portion 601 of the cable 60 may be seated in a recess 367 formed about the top surface of the access device 350. Alternatively, the branching portion may wrap around an outer surface of the side wall 340, or rest on the top surface of the side wall 340.

Alternatively, each light emitter 350 inserted in a lumen 348 may be separate and individually connected to a dedicated cable and/or light source, as shown in FIG. 7A.

Figure 8:
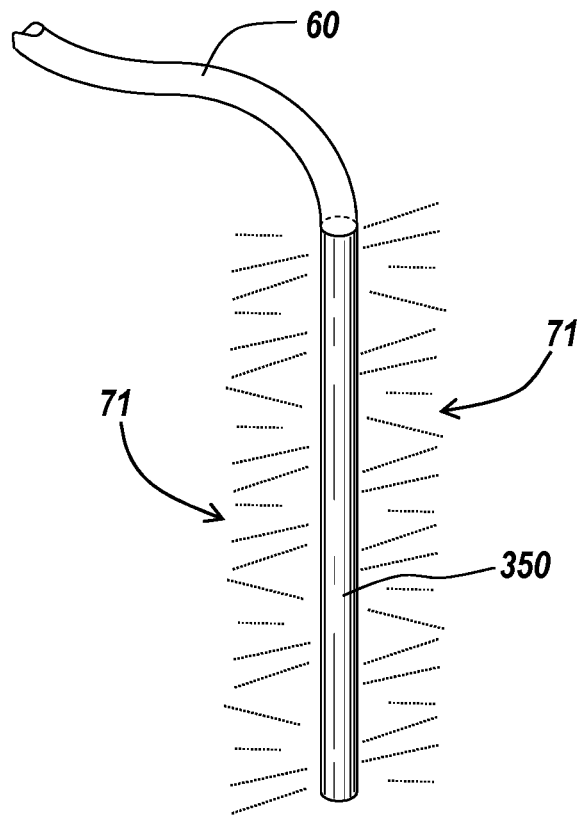
FIG. 8 illustrates an elongated light emitter suitable for use in the system of FIGS. 7A-7C.
Figure 9:
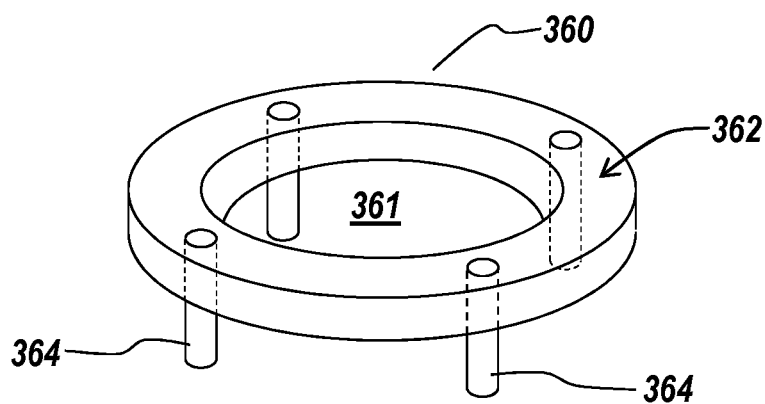
FIG. 9 illustrates a cover suitable for use with the illuminated surgical access system of FIGS. 7A-7C.

In the embodiments of FIGS. 7A-8, the elongated light emitter 350 and corresponding lumen 348 on the surgical access device 350 have substantially circular cross-sections, though, as described above, the cross-sections may have any suitable size and shape. In addition, the elongated light emitter 350 may have any suitable housing and light transmission element for emitting light from the elongated light emitter.

The illuminated surgical access system of the present invention may include a retention means for holding the elongated light emitter relative to a corresponding surgical access device. The retention means may also allow for adjustment of the position of the light emitter relative to the access device to control the direction and location of the emitted light.

Figure 10:
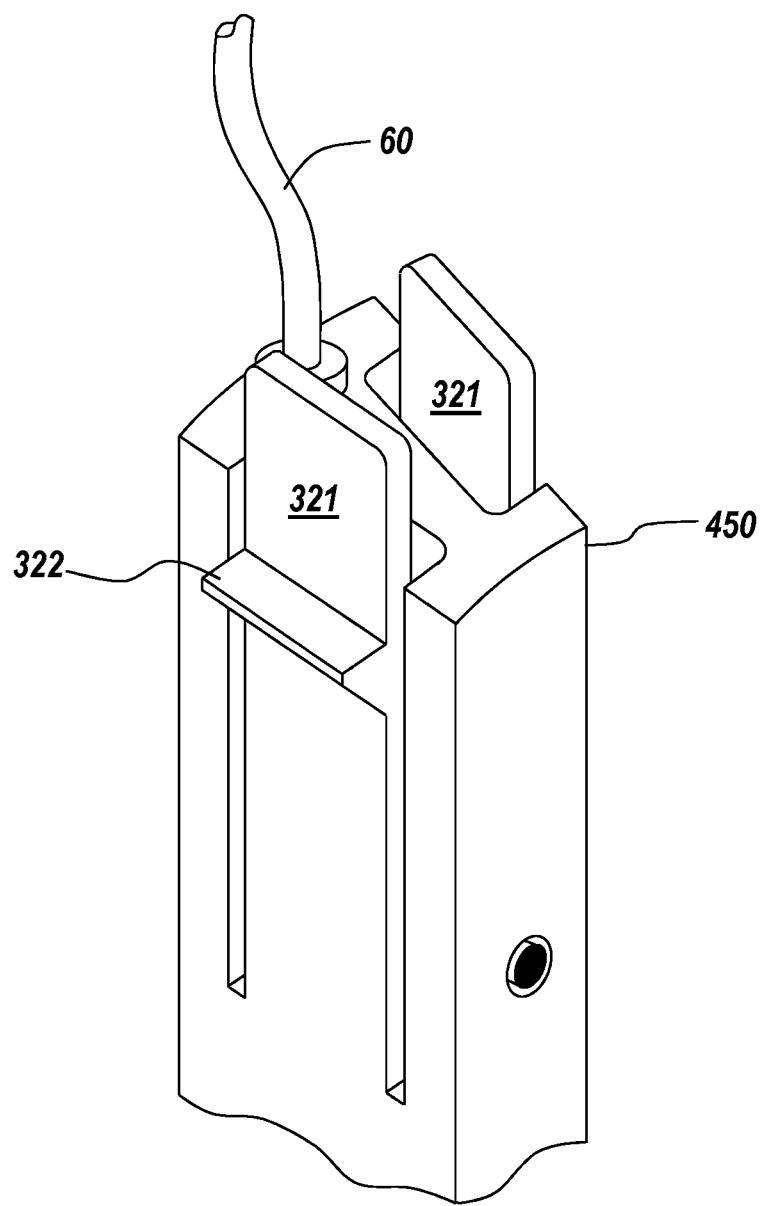
FIG. 10 illustrates an embodiment of a light-emitting shaft including tabs for securing the light-emitting shaft to a surgical access device.

For example, as shown in FIG. 10, the elongated light emitter-receiving channel and/or the elongated light emitter may include a ratcheting means for adjustably retaining the elongated light emitter in the channel. In the embodiment of FIG. 10, the elongated light emitter 450 includes spring loaded teeth 321 including protrusions 322 that engage corresponding notches in the elongated channel of the corresponding access device. The spring force of the teeth 321 keep the protrusions engaged in the channel and maintain the position of the light emitter 450 within the channel. A user can adjust the height of the light emitter within the channel by depressing the tabs to disengage the teeth from the notches, and then slide the light emitter 450 to a selected location in the channel.

One skilled in the art will recognize that any suitable means for releasably coupling an elongated light emitter to an access device may be used.

Figure 11A:
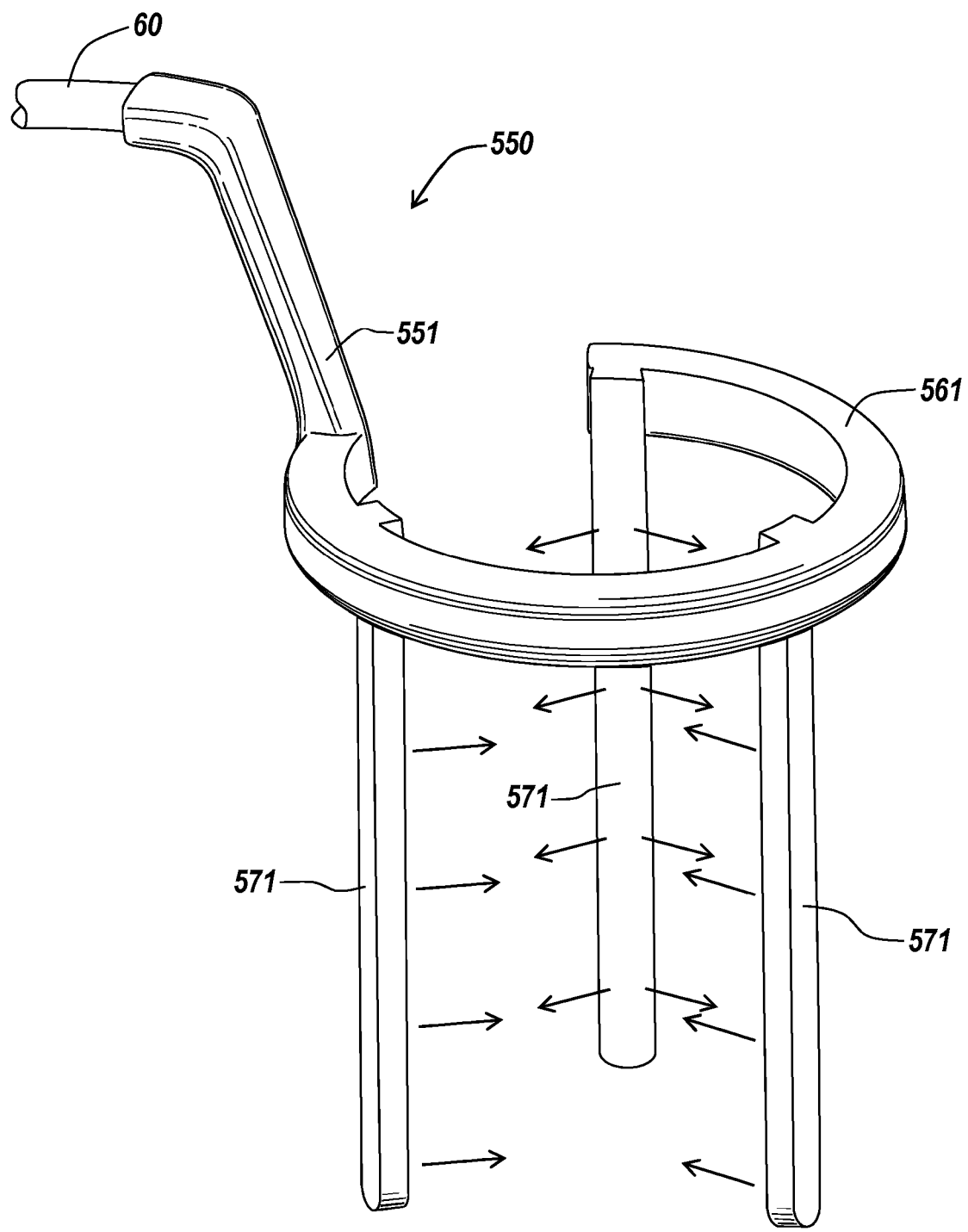
FIGS. 11A and 11B illustrate another embodiment of an elongated light emitter comprising a plurality of light-emitting protrusions extending from a base and a corresponding surgical access device according to another embodiment of the invention.
Figure 11B:
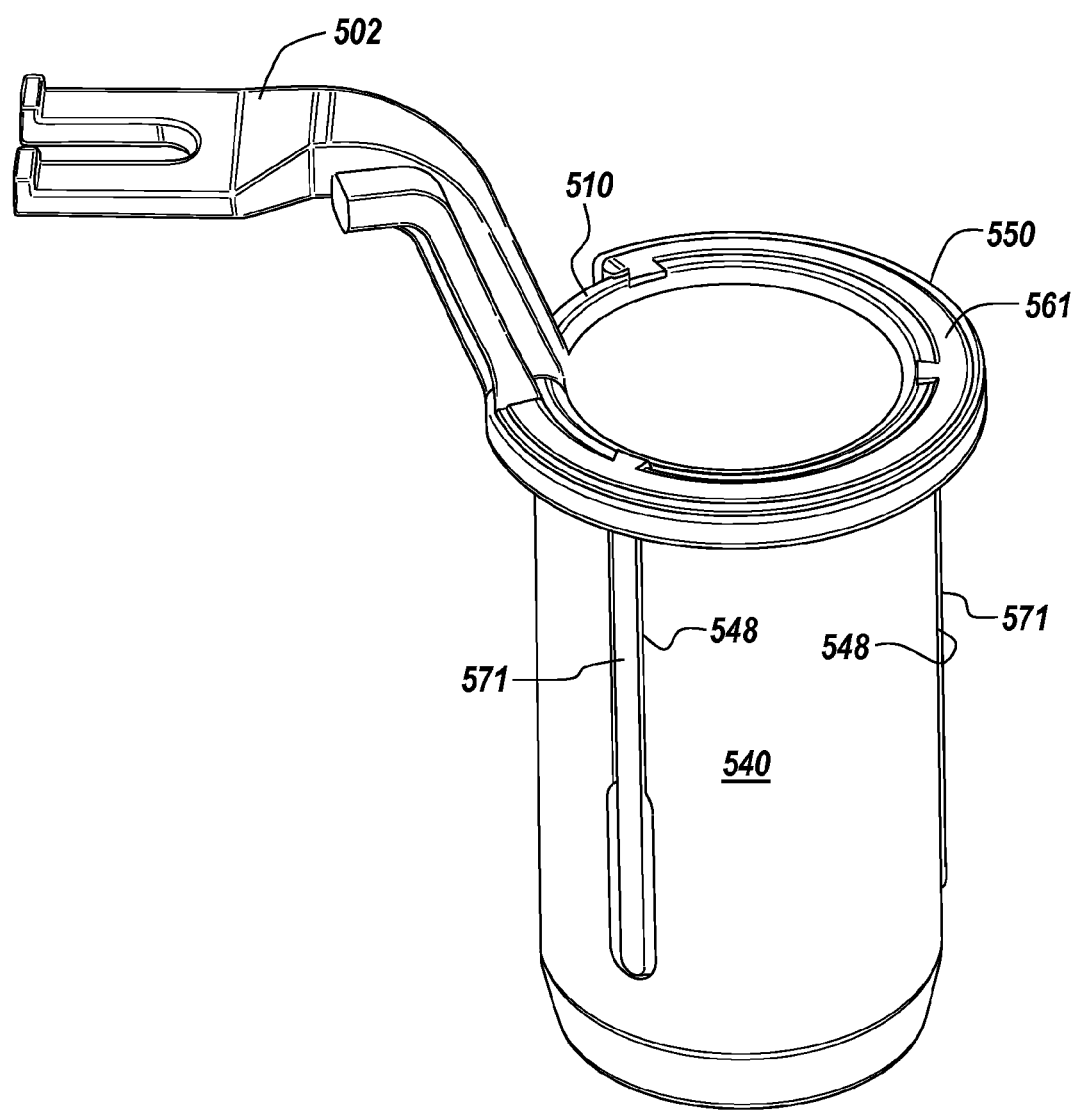

According to another embodiment of the invention, a light emitter can comprise a plurality of light-emitting shafts extending from a base. For example, as shown in FIGS. 11A and 11B, a light emitter 550 can comprise a housing 551 forming a ring-shaped base 561 and a plurality of protruding shafts 571 extending from the base 561. Each protruding shaft 571 is sized, spaced and configured to be received in a groove 548 on a corresponding access device 510 when the ring 561 is slipped over the proximal end of the access device, as shown in FIG. 11B. Each protruding shafts includes a light transmission element, such as a bundle of fiber optic strands, extending therethrough that may emit light 71.

The ring-shaped base 561 may be seated in a recess formed on the top proximal surface of the side wall 540, or may be seated flat against the top proximal surface. Alternatively, the ring may engage an outer surface of the side wall 540.

In the embodiment with of 11B, the light emitter 550 includes an arm attachment 502 for attaching the illuminated access system to a base or suitable system for allowing positioning of the illuminated surgical access system relative to a selected surgical site.

The protruding light-emitting shafts 571 may have any suitable configuration. For example, each protruding, light-emitting shaft 571 can be shaped like the light emitter 150 of FIGS. 2A and 2B or 3, with light emission along length of shaft, the light emitter 250 shown FIGS. 5A and 5B, with a single termination point, the rod-like configuration configured to be inserted through a side wall, as shown in FIGS. 7A-7B, or another configuration.

According to another embodiment of the invention, the elongated housing of a light emitter can be flexible and/or have a non-linear shape. For example, as shown in FIGS. 12A-12B, an elongated light emitter 650 can have a housing that is helical in shape. A corresponding access device 610 includes a helical channel 648 configured to receive the helical light emitter 650. The illustrative helical channel 648 is a groove formed on the exterior access device side wall 640. However, the helical channel 648 can alternatively be formed within the side wall 640, such that the light emitter is threaded into the channel. The channel 548 includes windows for transmitting light from a light emitter 650 received in the channel to the interior 642 of the access device 610.

The elongated helical light emitter 650 may have a plurality of light transmission elements, such as fiber optic cables, embedded therein for emitting light into the interior 642 of the access device 610. The fiber optic cables may have various termination points to emit light at different locations along the length of the light emitter 650, or may have a single termination point. Preferably, the termination points where light is emitted are equally spaced to prevent shadows.

Figure 13A:
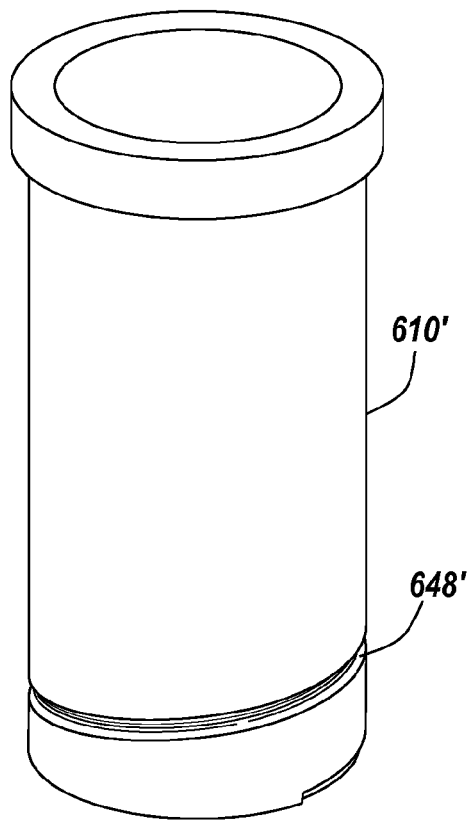
FIGS. 13A and 13B illustrate another embodiment of an elongated light emitter having a helical configuration and a corresponding surgical access device.
Figure 13B:
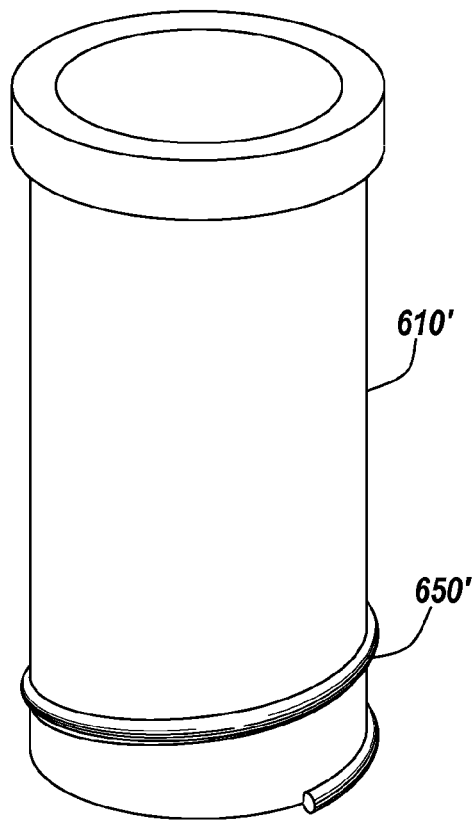

The helical channel 648 can be formed in any suitable location on the access device. For example, as shown in FIGS. 13A and 13B, the helical channel 648' can be disposed only on a distal end of the access device 610' for receiving a similarly-shaped light emitter 650' to emit light at the distal end, closer to the surgical site.

FIGS. 14A-14D illustrate still another embodiment of an elongated light emitter configured to be coupled to an access device. The light emitter 750 has a ring shape including one or more light transmission elements 752 matching an annular channel 748 formed at a lower end of the corresponding access device 710. The access device 710 can also include a longitudinal channel 762 extending through the side wall 740 of the access device 710 for passing cable, or another suitable light transmitter, to the ring-shaped channel 748. One or more windows 749 are provided in the annular channel 748 for passing light from a light emitter 750 inserted in the groove to the interior path 742 of the access device. Preferably, each light transmission element 752 aligns with a window 749 when the light transmitter 750 is inserted in the channel 748.

According to still another embodiment of the invention, shown inn FIGS. 15A-15B, the housing 851 of an elongated light emitter 850 can form a portion of the side wall 840 of the access device 810. For example, the access device 810 may comprise an annular base 812, with a substantially tubular side wall 840 that is not fully closed and includes a channel formed by gap 814 between edges 840a and 840b of the side wall 840. The light emitter 850 may be shaped to fit into the gap 814 to complete the side wall and remain in place during the subsequent surgical procedure. In this embodiment, the window for transmitting light from a light emitter to the interior 842 and the elongated channel for receiving the light emitter comprise the same element and light emitted from the light emitter 850 is immediately directed into the access device interior 842. As shown, the annular base 812 of the access device 810 may include a recess 816 or other suitable means for retaining the light emitter. The light emitter 850 may releasably engage the edges 840a, 840b of the side wall 840 through any suitable means.

In the embodiment of FIG. 15B, the light emitter 850 includes an arm attachment 802 for attaching the illuminated access system to a base or suitable system for allowing positioning of the illuminated surgical access system relative to a selected surgical site.

One skilled in the art will recognize that the access device 810 may include a plurality of openings for receiving a plurality of light emitters 850 that complete the side wall 840 and provide illumination of the device interior.

In still another embodiment, a light emitter can comprise a light emitting ring that fits into a recess in the inner surface of the access device, as shown in FIGS. 16A-16D. The illustrative light emitter 950 comprises an annular housing 951 including an annular groove 959 formed on a bottom surface for receiving a bundle of fiber optic cables or other suitable light transmission element. The termination points of the fiber optic cables are preferably distributed about the groove 959 to distribute light transmitted through the fiber optic cables radially. The housing 951 may also include an exit hole 962 for connecting the fiber optic cables to a light source, which provides light that is transmitted through and emitted by the fiber optic cables.

Figure 16A:
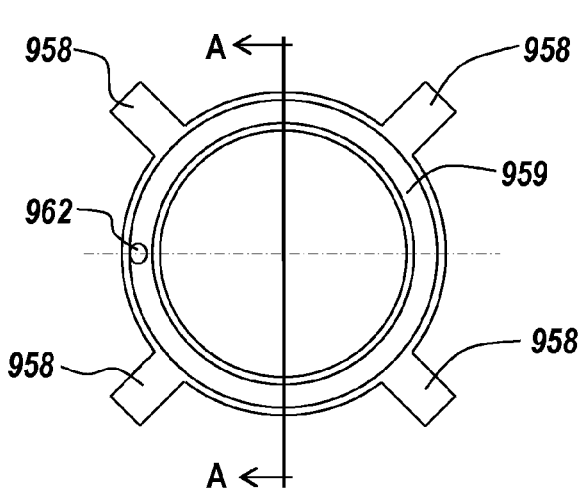
FIGS. 16A-16D illustrate an annular elongated light emitter configured to be received in an interior channel of a surgical access device according to another embodiment of the invention.
Figure 16B:
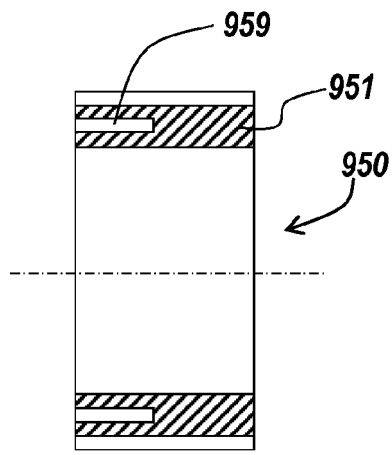
Figure 16C:
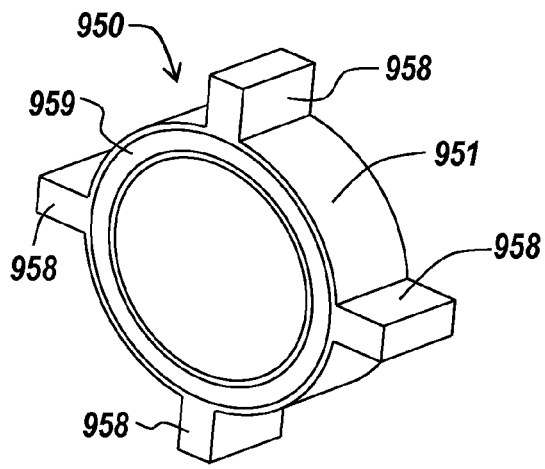
Figure 16D:
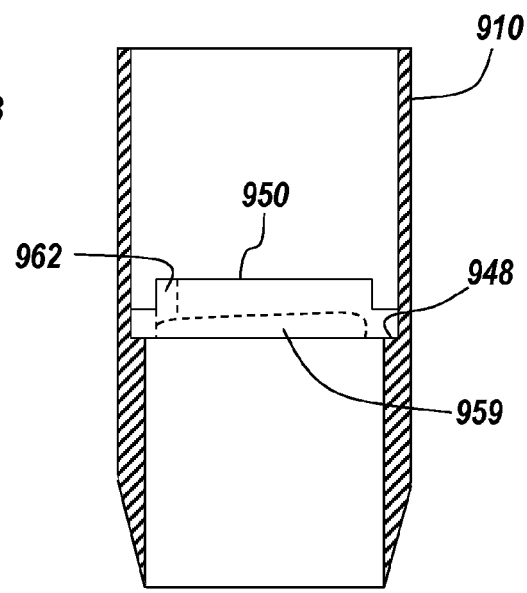

As shown in FIG. 16D, the annular light emitter is preferably coupled to an interior channel 948 of a corresponding access device 910. The illustrative channel 948 may be formed by a plurality of interior slots configured to receive protrusions 958 extending from the annular base of the light emitter 950. The protrusions 958 are sized and dimensioned to be received in the slots to couple the annular light emitter 950 to the access device 910. Alternatively, the interior channel 948 may comprise a shelf formed about the inner diameter of the access device 910. In this manner, the light emitter provides light radially about the interior path 942 of the access device 910.

As described above, the access device 10 forming the illuminated surgical access system provides working channel from the skin proximate vertebrae to perform a procedure at or near the vertebrae. An example of a suitable access device is the PIPELINE® discectomy port available from DePuy Spine, Inc of Raynham, Mass., though any suitable access device may be used.

The access device 10 forming the illuminated surgical access system can be spaced from or directly interface with a surgical site. The distal end 47 of the tubular body can be configured to interface with bone or another feature to facilitate positioning of the tubular body along a suitable trajectory relative to the surgical site. For example, the distal end 47 may shaped to engage a part of the surgical site, such as a vertebral structure, and can optionally include teeth or other suitable feature formed on an outer surface for engaging a part of the surgical site, such as a vertebra.

The tubular body 40 of the illustrative access device 10 can be rigid, semi-rigid or flexible, and can have any suitable size, shape and configuration suitable for defining a working channel and/or access to a surgical site. In the illustrative embodiment, the tubular body is straight to define a straight channel therethrough, though one skilled in the art will recognize that the tubular body may define a shaped trajectory therethrough. The tubular body is not limited to a tubular structure having closed sidewalls and can be any component that defines a path, including an open channel or a solid member.

The path through the access device may also or alternatively form a working channel configured to receive selected surgical instruments, such as awls, bone taps, obturators, drills, guide wires, and/or implants, such as screws, fusion devices, artificial disks and hip stems, along the longitudinal axis thereof.

In one embodiment, the illuminated access device 10 may be configured to guide instruments along the working channel. In such an embodiment, the inner diameter of the tubular body may be slightly larger than the outer diameter of the instrument guided by the tubular body, so that the instrument can be inserted through the tubular body while the sidewalls of the tubular body maintain the instrument at a predetermined angle relative to the patient. Alternatively, an instrument to be guided by the tubular body can be configured to slide over the tubular body, with the tubular body maintaining the orientation of the instrument as the instrument slides relative to the tubular body. In this embodiment, the tubular body can have an outer diameter that is slightly less than an inner diameter of an instrument. However, the access device 10 need not form a trajectory or guide for instruments and can be any device suitable for providing access to a surgical site.

The use of an elongated light emitter configured to be coupled to a surgical access device via a channel formed on the surgical access device provides significant advantages over prior systems for providing illumination during a surgical procedure. The elongated light emitter easily integrates illumination into a surgical access device, without requiring cumbersome cables, while allowing direction of light to an ideal location. The elongated light emitter may be moved or adjusted to adjust the location and direction of the emitted light relative to the surgical site and or working channel. The elongated light emitter does not compromise or reduce the working area, as it is coupled to a channel in the side wall of the surgical access device, and provides superior illumination. In addition, the elongated light emitter may be easily removed or decoupled from a surgical access device to allow reuse, disposal or cleaning. In this manner, the elongated light emitter of the illustrative embodiments of the invention provides enhanced illumination during many types of surgical procedures.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. A lighted surgical access system for providing access to a patient, comprising:
    a surgical access device having a sidewall and an elongated opening in an outer surface of the sidewall that extends substantially parallel to a longitudinal axis of the surgical access device, wherein the surgical access device defines a port to a surgical site and includes an open distal end;
    an elongated light emitter that couples to the surgical access device by sliding into the elongated opening, the elongated light emitter including a bundle of fiber optic strands defining a branched path that terminates in a plurality of outlets and a housing for the bundle of fiber optic strands; and
    wherein the elongated opening includes windows, wherein each window aligns with a corresponding one of the outlets of the branched path to transfer light to an interior of the surgical access device.

2. The lighted surgical access system of claim 1 wherein the elongated opening extends from a proximal end of the surgical access device to a distal end of the surgical access device.

3. The lighted surgical access system of claim 1 wherein the elongated light emitter is substantially straight.

4. A lighted surgical access port for illuminating a working area on a patient, comprising:
    a hollow tubular body having a central lumen and an open distal end;
    a groove extending along an outer surface of the tubular body, wherein the groove extends along a longitudinal axis of the hollow tubular body;
    an elongated light emitter for being slidably inserted into the groove, the light emitter including a bundle of fiber optic strands defining a branched path that terminates in a plurality of outlets and a housing for the bundle of fiber optic strands; and
    wherein the groove includes windows, wherein each window aligns with a corresponding one of the outlets of the branched path to transfer light to the interior of the surgical access device.

5. The lighted access port of claim 4 wherein a cross-section of the light emitter is wedge-shaped.

6. The light access port of claim 4 further comprising:
    an additional groove formed in the outer surface of the tubular body; and
    an additional light emitter inserted in the additional groove for providing additional illumination of the working area, wherein the additional light emitter includes, a light transmitting element.

7. The lighted access port of claim 4 wherein the light emitter is straight along a length of the light emitter.

8. The lighted access port of claim 4 wherein a shape of the groove matches a shape of the light emitter.

9. The lighted access port of claim 4 wherein the groove extends substantially parallel to a longitudinal access of the hollow tubular body.

* * * * *